US00PP35705P2

(12) United States Plant Patent
Brouwer

(10) Patent No.: US PP35,705 P2
(45) Date of Patent: Mar. 26, 2024

(54) ***SPATHIPHYLLUM* PLANT NAMED 'BROJEDIABO'**

(50) Latin Name: ***Spathiphyllum* sp. Schott.**
Varietal Denomination: BROJEDIABO

(71) Applicant: ISB Holland B.V., Nootdorp (NL)

(72) Inventor: Wim A. J. Brouwer, Nootdorp (NL)

(73) Assignee: Van der Voort Young Plants B.V., Honselersdijk (NL)

( * ) Notice: Subject to any disclaimer, the term of this patent is extended or adjusted under 35 U.S.C. 154(b) by 0 days.

(21) Appl. No.: 18/445,182

(22) Filed: May 15, 2023

(51) Int. Cl.
*A01H 5/12* (2018.01)
*A01H 6/10* (2018.01)

(52) U.S. Cl.
USPC ..... Plt./364

(58) Field of Classification Search
USPC ..... Plt./364
See application file for complete search history.

*Primary Examiner* — Susan McCormick Ewoldt
*Assistant Examiner* — Zachariah Allan Kay
(74) *Attorney, Agent, or Firm* — Samuel R. McCoy, Jr.

(57) ABSTRACT

'BROJEDIABO' is a new and distinctive variety of *Spathiphyllum* plant which is characterized by a fast rate of growth, a compact and densely foliaged growth habit, thin foliage which is soft to the touch, variegated foliage that is green and dotted, mottled and streaked with a combination of light white and light greyed-green at maturity, and the stability of all characteristics from generation to generation.

2 Drawing Sheets

Latin name of the genus and species: The Latin name of the genus and species of the novel variety disclosed herein is *Spathiphyllum* sp. Schott.

Variety denomination: The inventive variety of *Spathiphyllum* disclosed herein has been given the variety denomination 'BROJEDIABO'.

BACKGROUND OF THE INVENTION

Parentage: The new plant is a seedling selection which resulted from the controlled pollination of the proprietary seed parent, *Spathiphyllum* sp. 'SP6527' (not patented), and the proprietary pollen parent, *Spathiphyllum* sp. 'SP6578' (not patented). Both parents, which exhibited a compact, densely foliaged habit and non-variegated foliage, were developed and owned by the inventor and were never commercially released. Said cross was performed by the inventor at a commercial greenhouse in Nootdorp, The Netherlands in August of 2013. Seeds from said cross were harvested, then germinated, and the resulting seedlings were grown to a mature size in order to evaluate for desirable commercial characteristics. In September of 2014, the inventor selected the claimed *Spathiphyllum* plant for commercialization due to its compact, densely-foliaged growth habit, vigorous growth, and unique, stable variegation. The new plant was given the variety denomination 'BROJEDIABO'.

Asexual Reproduction: Asexual reproduction of 'BROJEDIABO', by way of meristematic tissue culture, was first performed in October of 2014 at a commercial laboratory in Evergem, Belgium. Nine successive generations so produced have shown that the unique features of the instant cultivar are stable and reproduced true to type.

SUMMARY OF THE INVENTION

The cultivar 'BROJEDIABO' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Spathiphyllum* plant, 'BROJEDIABO'. These traits, in combination, distinguish 'BROJEDIABO' as a new and distinct cultivar:

1. *Spathiphyllum* 'BROJEDIABO' exhibits a compact, densely foliaged growth habit which is suitable for production in relatively small nursery containers; and
2. *Spathiphyllum* 'BROJEDIABO' exhibits a fast rate of growth; and
3. *Spathiphyllum* 'BROJEDIABO' exhibits thin foliage which is soft to the touch; and
4. *Spathiphyllum* 'BROJEDIABO' exhibits strongly variegated mature foliage that is very heavily and irregularly dotted, mottled, and streaked with a combination of yellow-green and greyed-green in a pattern that follows the secondary lateral veins.

BRIEF DESCRIPTION OF THE FIGURES

The photographs were taken using conventional techniques and although colors may appear different from actual colors due to light reflectance it is as accurate as possible by conventional photographic techniques.

BOTANICAL DESCRIPTION OF THE PLANT

Figure 1:
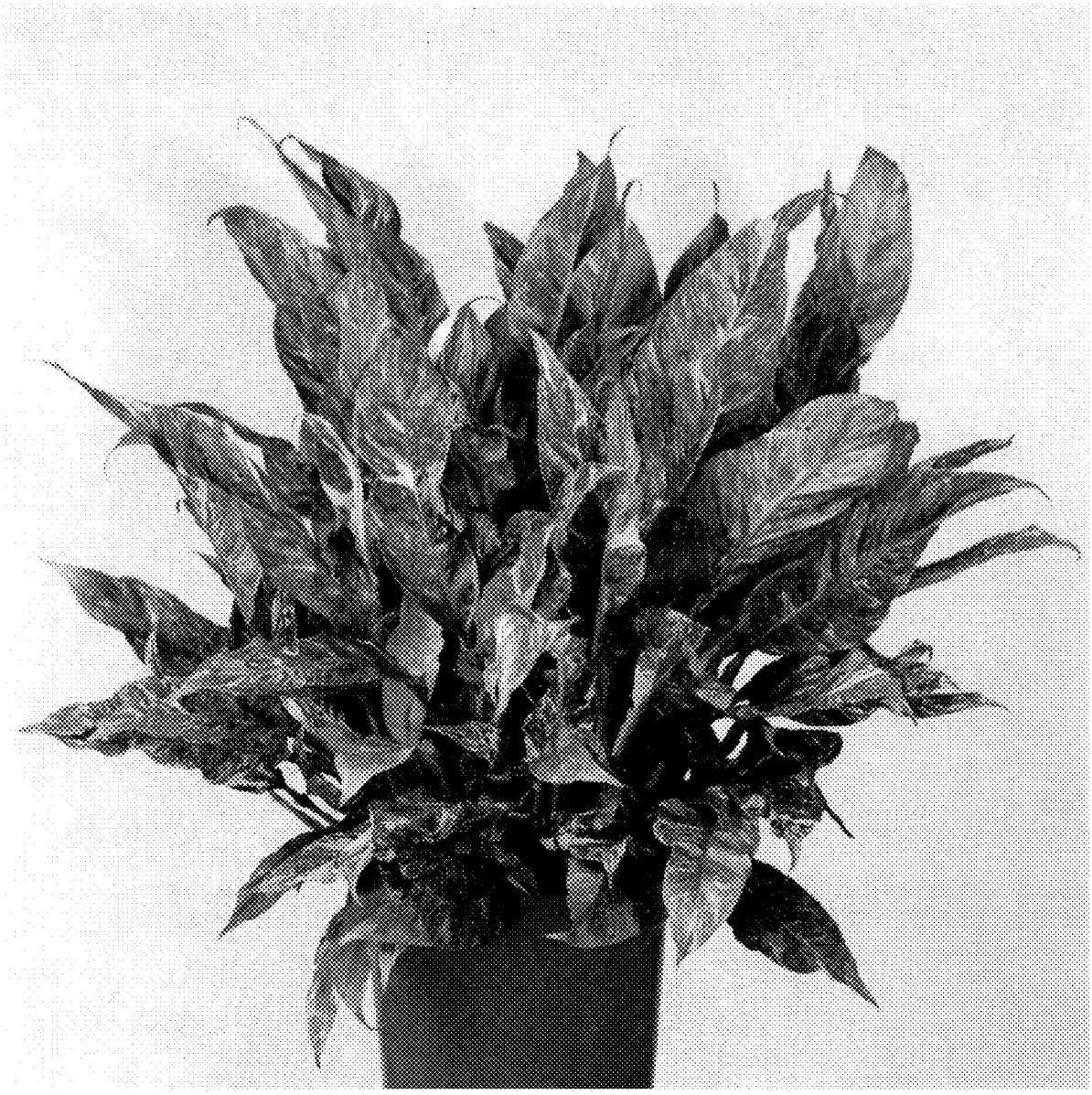
FIG. 1 shows, as nearly true as it is reasonably possible to make the same in color illustrations of this type, an exemplary 'BROJEDIABO' plant. The plant shown is approximately 12 months old from a rooted cutting, potted into a 27 cm nursery pot, grown in a climate-controlled greenhouse in Nootdorp, the Netherlands.
Figure 2:
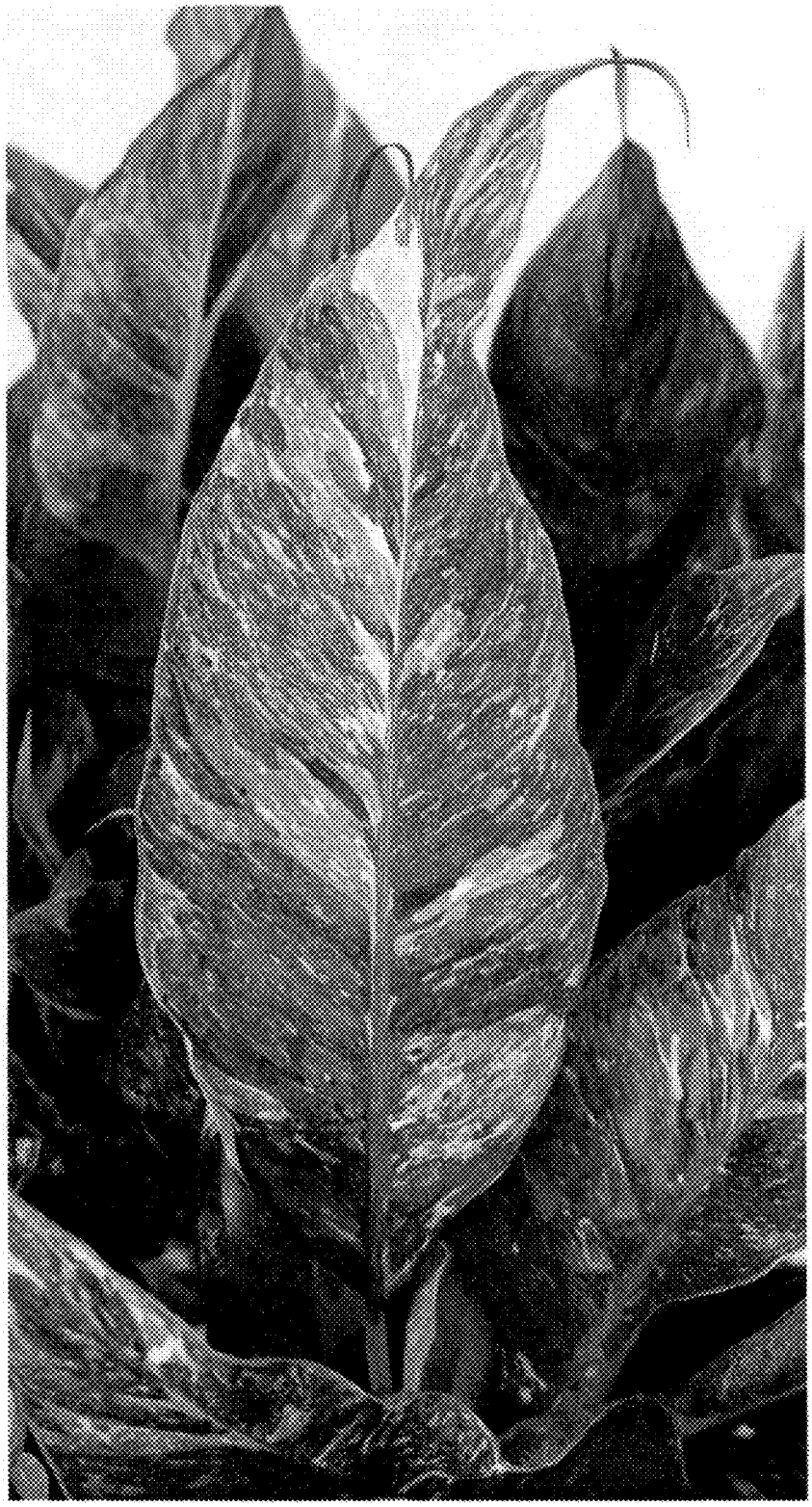
FIG. 2 shows, as nearly true as it is reasonably possible to make the same in color illustrations of this type, the typical foliage of the plant in FIG. 1.

The following observations and measurements made in January of 2023 describe averages from a sample set of six specimens of 1 year old 'BROJEDIABO' plants grown in 27 cm nursery containers at commercial greenhouse in Nootdorp, the Netherlands. Plants were produced using conventional greenhouse production protocols for *Spathiphyllum*. Temperatures ranged from 18 to 22 degrees Celsius, both night and day. No chemical pest and disease control measures were taken. No photoperiodic treatments or artificial light was given to the plants.

Those skilled in the art will appreciate that certain characteristics will vary with older or, conversely, with younger plants. 'BROJEDIABO' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, Sixth Edition.

A botanical description of 'BROJEDIABO' and comparisons with the parents and the most similar variety of common knowledge are provided below.

General plant description:

*Growth habit.*—Clumping herbaceous perennial; broad spreading to upright with foliage arising directly from the base of each clump.

*Plant profile.*—Near globular.

*Height.*—64.6 cm in height, to the highest leaf.

*Width.*—Average 87.5 cm in width.

*Growth rate.*—Moderately fast growing.

*Plant vigor.*—Moderately to highly vigorous.

*Propagation.*—Method — Meristematic tissue culture. Time to initiate roots — Approximately 18 days to initiate roots at an approximate soil temperature of 25 degrees Celsius. Crop time — Approximately 14 weeks to produce a well-rooted cutting at an approximate soil temperature of 20 to 30 degrees Celsius.

*Environmental tolerances.*—Moderately high tolerance to rain and wind; tolerant of temperatures ranging from 5 to 40 degrees Celsius. Cold hardy to USDA Hardiness Zone 10.

*Pest resistance and susceptibility.*—Plants have not been observed to be any more or less susceptible or resistant to pathogens and pests common to *Spathiphyllum*.

Root system:

*General.*—Thick, fleshy roots with fine, fibrous lateral roots.

*Distribution in the soil profile.*—Shallow to moderately deep.

*Texture.*—Smooth; glabrous.

*Color.*—Orange-white, nearest to RHS 158C.

Stems:

*Branching characteristics.*—Clumping plant with leaves emerging directly from the base of the plant; no lateral branching.

Foliage:

*Arrangement.*—Alternate; equitant.

*Division.*—Simple.

*Attachment.*—Petiolate.

*Quantity of leaves per shoot.*—Average of 6.

*Quantity of shoots per plant.*—Average of 18.

*Quantity of leaves per plant.*—Approximately 110.

*Lamina.*—Shape — Narrow ovate to narrow elliptic to near-oblong. Apex — Narrow apiculate. Base — Attenuate. Aspect — Slightly carinate; moderately to strongly reflexed; occasionally spiraled. Attitude — Younger foliage at the center of the plant is held upright; older foliage is more relaxed. Dimensions — 33.6 cm long and 11.4 cm wide. Margin — Entire; moderately undulate. Texture and luster, adaxial surface — Moderately rugose, glabrous, and slightly glossy. Texture and luster, abaxial surface — Moderately rugose, glabrous, and moderately glossy. Juvenile color, adaxial surface — Yellow-green, nearest to in between RHS 144A and N144C; very heavily and irregularly dotted, mottled, and streaked with a combination of yellow and yellow-green in a pattern that follows the secondary lateral veins, nearest to RHS 4B, 144B, 144C, 145D, 154C, and 154D. Juvenile color, abaxial surface — Yellow-green, nearest to in between RHS 144A and 144B; very heavily and irregularly dotted, mottled, and streaked with a combination of yellow and yellow-green in a pattern that follows the secondary lateral veins, nearest to RHS 4C, 145C, 145D, and 154D. Mature color, adaxial surface — A mixture of green and yellow-green, nearest to RHS NN137A and 147A; very heavily and irregularly dotted, mottled, and streaked with a combination of white and greyed-green in a pattern that follows the secondary lateral veins, nearest to RHS 155C, 189A, 189B, 191A, and 191B. Mature color, abaxial surface — Yellow-green, nearest to RHS 147A; very heavily and irregularly dotted, mottled, and streaked with a combination of yellow-green and greyed-green in a pattern that follows the secondary lateral veins, nearest to RHS 146A, 155B, 155C, 188A, 188B, 189A, 189B, and N189D. Venation — Vein pattern — Pinnate. Vein color, adaxial surface — Green, nearest to RHS 137B, and axially striped greyed-green, nearest to in between RHS 193B and 193C. Vein color, abaxial surface — Yellow-green, nearest to RHS 144B, and axially striped with a lighter shade of yellow-green, nearest to RHS N144D.

*Petiole, including geniculum.*—Length — Approximately 25.8 cm. Width — 1.0.cm, proximally; 0.5 cm distally. Texture and luster — Smooth, glabrous, and very slight glossy. Strength — Strong. Color, adaxial surface — Yellow-green, nearest to RHS 145C. Color, abaxial surface — Green, nearest to RHS 137A, and axially striped yellow-green, nearest to RHS 144A. Geniculum — Length — Approximately 3.5 cm. Width — Approximately 0.65 cm. Texture and Luster — Smooth, glabrous and matte. Color — Green, nearest to in between RHS 137B and 137C; axially striped yellow-green, nearest to in between RHS 144A and 144B. Petiole wings — Length — Approximately 22.3 cm. Width — Approximately 0.9 cm. Color, adaxial surface — Yellow-green, nearest to a mixture of RHS 146A and 147B; axially striped green-white, nearest to RHS 157B. Color, abaxial surface — Yellow-green, nearest to RHS 147A; axially striped with a combination yellow-green and green-white, nearest to RHS145C, 145D, and 157A.

Inflorescence: *Spathiphyllum* sp. typically produces a spathe, and spadix inflorescence, but no flowering of the claimed plant has been observed to date.

Spathe: To date, no flowering has been observed.

Spadix: To date, no flowering has been observed.

Reproductive organs: To date, no flowering has been observed.

Seed and fruit: Seed production has not been observed.

Comparisons with the parent: Plants of the new cultivar 'BROJEDIABO' may be distinguished from the seed parent, *Spathiphyllum* sp. 'SP6527' (not patented), by the following combination of characteristics described in Table 1.

TABLE 1

| Characteristic | 'BROJEDIABO' | 'SP6527' |
|---|---|---|
| Foliage shape. | Narrow ovate to narrow elliptic to near-oblong. | Ovate. |
| Foliar margins. | Moderately undulate. | Undulate. |
| Foliage variegation. | Present. | Absent. |

Plants of the new cultivar 'BROJEDIABO' may be distinguished from the pollen parent, *Spathiphyllum* sp. 'SP6578' (not patented) by the following combination of characteristics described in Table 2.

TABLE 2

| Characteristic | 'BROJEDIABO' | 'SP6578' |
|---|---|---|
| Foliage variegation. | Present. | Absent. |
| Foliage shape. | Narrow ovate to narrow elliptic to near-oblong. | Narrow elliptic. |
| Foliage variegation. | Present. | Absent. |

Comparisons with the most similar variety of common knowledge: Plants of the new cultivar 'BROJEDIABO' may be distinguished from the commercial variety, *Spathiphyllum* sp. 'SP7018' (U.S. Plant Pat. No. 33,426), by the following combination of characteristics described in Table 3.

TABLE 3

| Characteristic | 'BROJEDIABO' | 'SP7018' |
|---|---|---|
| Plant size. | Larger than 'SP7018'. | Smaller than 'BROJEDIABO'. |
| Foliage abundance. | More abundant than 'SP7018'. | Less abundant than 'BROJEDIABO'. |
| Foliage shape. | Narrow ovate to narrow elliptic to near-oblong. | Narrow ovate to narrow elliptic. |
| Foliage size. | Larger than 'SP7018' | Smaller than 'BROJEDIABO'. |
| General coloration of the juvenile adaxial foliar surface. | Yellow-green; very heavily and irregularly dotted, mottled, and streaked with a combination of yellow and yellow-green. | A mixture of green and yellow green; heavily, irregularly mottled and streaked with a combination of white, green-white and greyed-green. |
| General coloration of the mature adaxial foliar surface. | A mixture of green and yellow-green; very heavily and irregularly dotted, mottled, and streaked with a combination of white and greyed-green. | Green; heavily, irregularly mottled and streaked with a combination of white, green-white and greyed-green. |
| Prominence of foliage variegation. | More prominent than 'SP7018'. | Less conspicuous than 'BROJEDIABO'. |

That which is claimed is:

1. A new and distinct variety of *Spathiphyllum* plant named 'BROJEDIABO', substantially as described and illustrated herein.

* * * * *